United States Patent

Smethers et al.

Patent Number: 6,102,907
Date of Patent: *Aug. 15, 2000

[54] APPARATUS AND DEVICE FOR USE THEREIN AND METHOD FOR ABLATION OF TISSUE

[75] Inventors: Rick T. Smethers, Fremont; James A. Filice; Kirti P. Kamdar, both of Sunnyvale; Peter H. Muller, Los Gatos, all of Calif.

[73] Assignee: Somnus Medical Technologies, Inc., Sunnyvale, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/912,273

[22] Filed: Aug. 15, 1997

[51] Int. Cl.⁷ .................................................. A61B 18/18
[52] U.S. Cl. ................................ 606/40; 606/41; 606/49
[58] Field of Search ........................... 606/40–42, 45–52; 604/192, 263

[56] References Cited

U.S. PATENT DOCUMENTS

| | | | |
|---|---|---|---|
| 1,279,530 | 9/1918 | Fitting . | |
| 3,401,693 | 9/1968 | Cohen . | |
| 4,032,738 | 6/1977 | Esty et al. . | |
| 5,089,002 | 2/1992 | Kirwan | 606/50 |
| 5,281,218 | 1/1994 | Imran | 606/41 |
| 5,366,476 | 11/1994 | Noda | 606/206 |
| 5,403,311 | 4/1995 | Abele et al. | 606/49 |
| 5,413,575 | 5/1995 | Haenggi | 606/45 |
| 5,514,131 | 5/1996 | Edwards et al. | 606/45 |
| 5,536,267 | 7/1996 | Edwards et al. | 606/41 |
| 5,542,915 | 8/1996 | Edwards et al. | 604/22 |
| 5,599,345 | 2/1997 | Edwards et al. | 606/41 |
| 5,693,044 | 12/1997 | Cosmescu | 606/42 |
| 5,814,043 | 9/1998 | Shapeton | 606/48 |

*Primary Examiner*—Linda C. M. Dvorak
*Assistant Examiner*—Roy Gibson
*Attorney, Agent, or Firm*—Flehr Hohbach Test Albritton & Herbert LLP

[57] ABSTRACT

A device for the ablation of tissue for use with the human hand and a radio frequency power supply and controller providing a source of radio frequency energy and a control for controlling the application of radio frequency energy to the device. The device includes a handle sized so that is adapted to be grasped by the human hand and has proximal and distal extremities. A needle formed of a conducting material has proximal and distal extremities. The proximal extremity of the needle is mounted on the distal extremity of the handle so that it is insulated from the handle. Conductors are carried by the handle and are connected to the needle and extend from the handle and are coupled to the radio frequency power supply and controller for supplying radio frequency energy to the needle. A temperature sensor is carried by the handle and is adapted to be coupled to the radio frequency power supply and controller for sensing the application of radio frequency energy to the tissue for controlling the application of radio frequency energy to the needle.

13 Claims, 2 Drawing Sheets

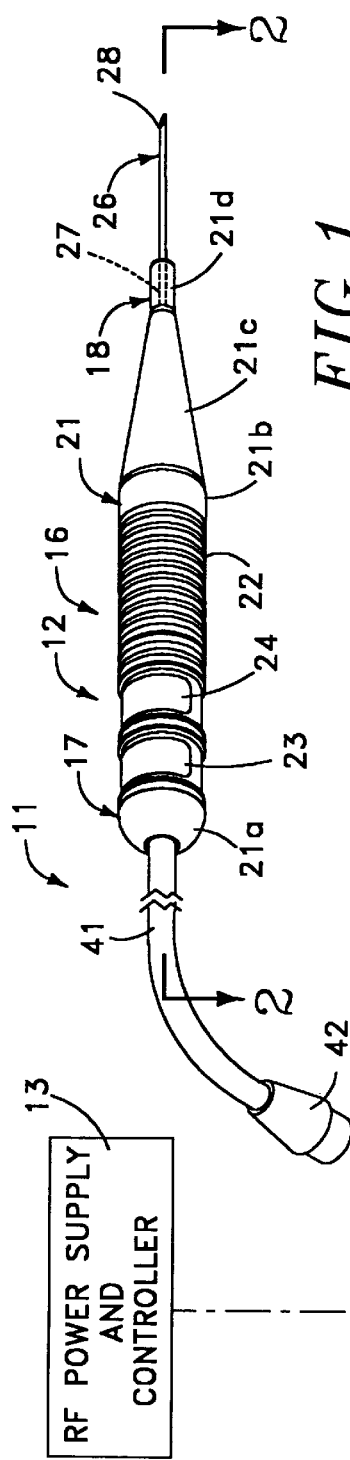
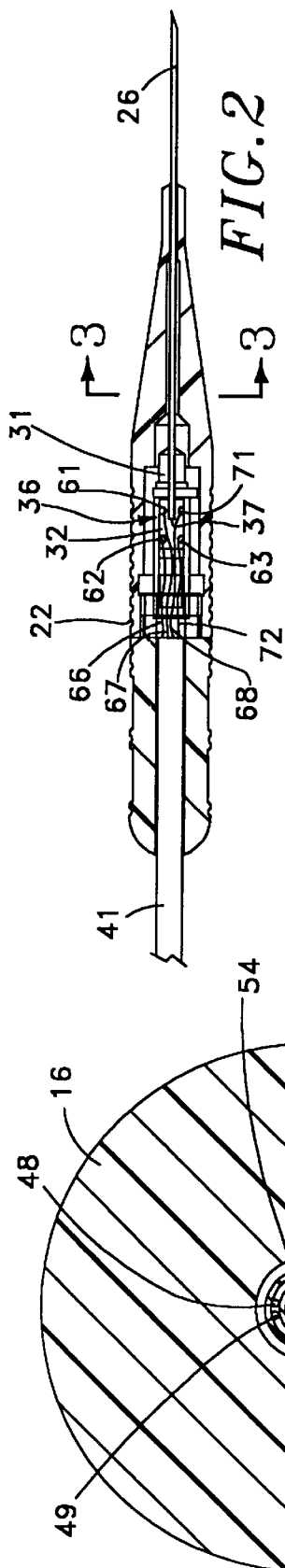
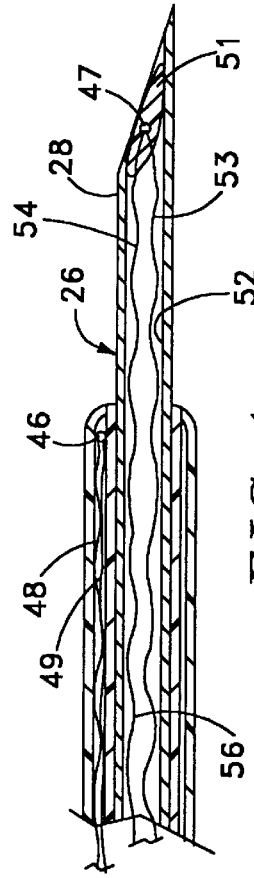
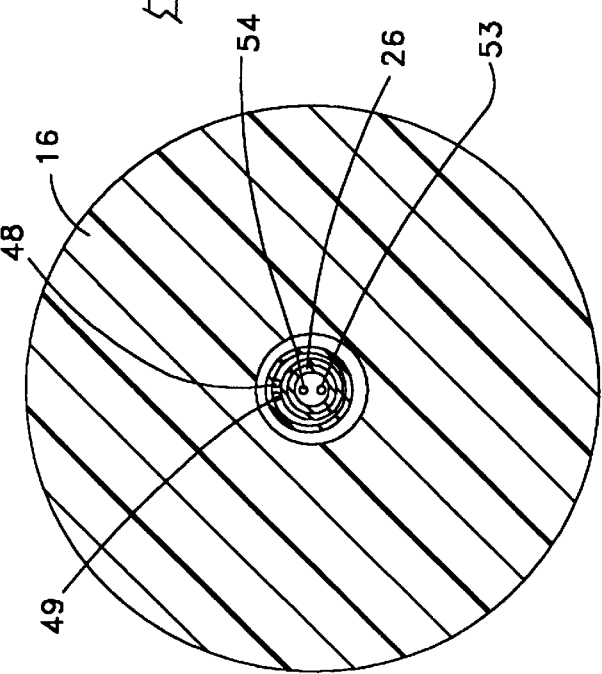

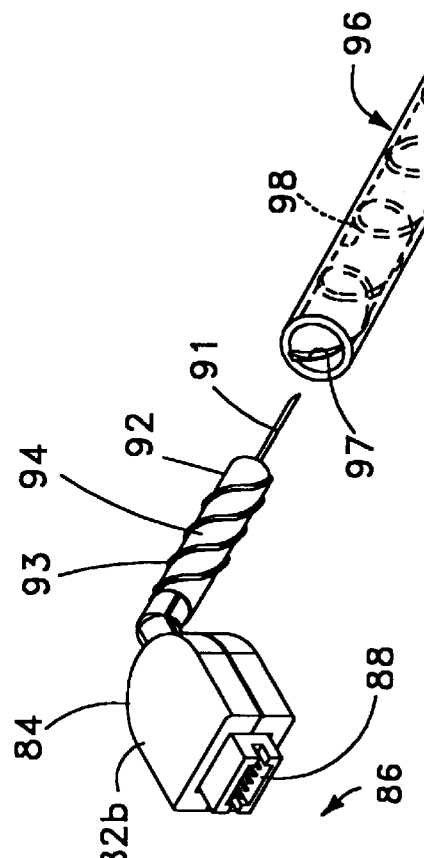
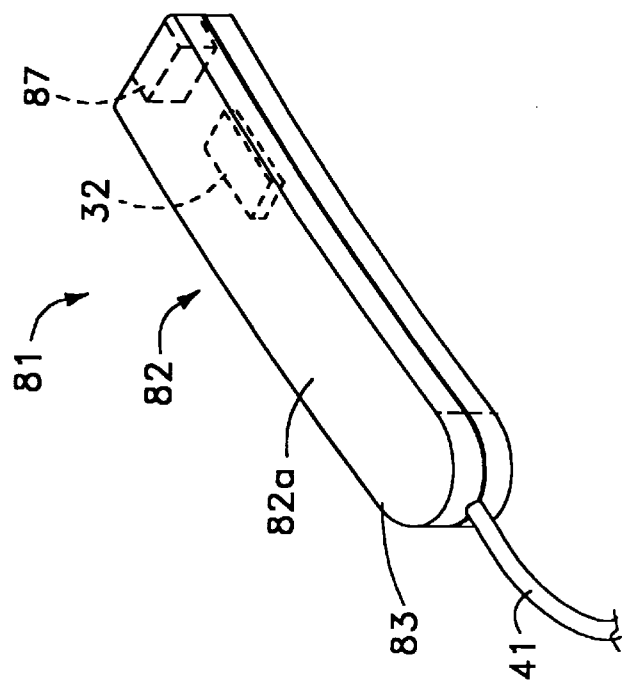
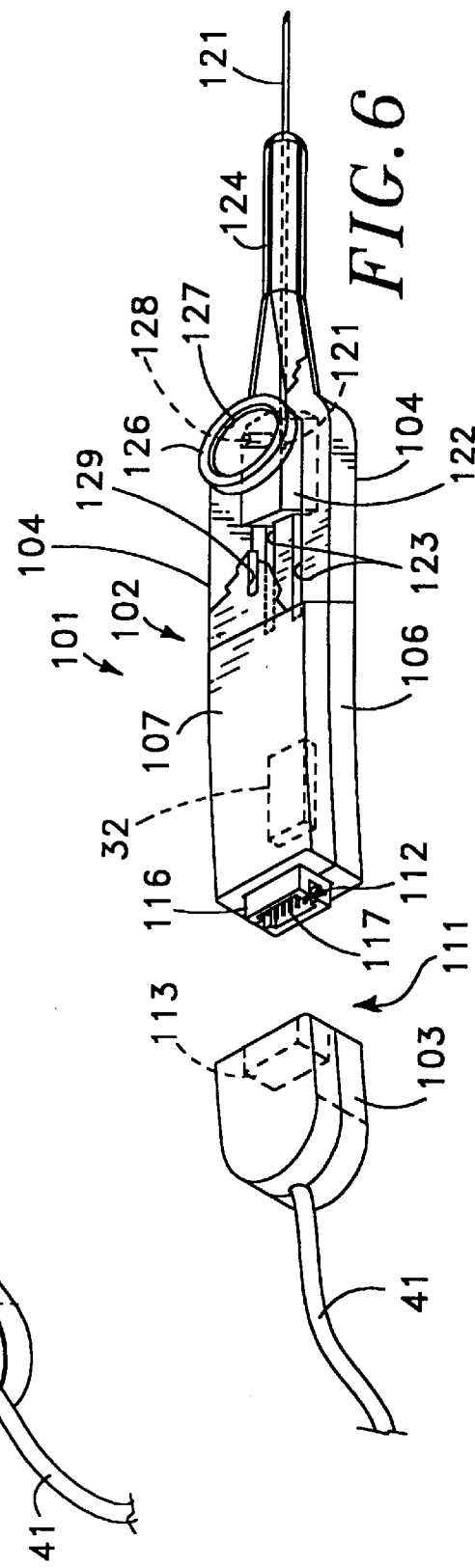
FIG. 5
FIG. 6

APPARATUS AND DEVICE FOR USE THEREIN AND METHOD FOR ABLATION OF TISSUE

This invention relates to an apparatus and device for use therein and a method for ablation of tissue and more particularly to the treatment of tissue in the human body as for example the uvula, tonsils, adenoids, sinus tissue, tongue and turbinates.

Apparatus, device for use therein and methods for ablating tissue have heretofore been provided. However it has been found that for some applications, they are unduly complicated and expensive. There is therefore a need for a simplified tissue ablation device which will meet the requirements for tissue ablation and be less expensive.

In general it is an object of the present invention to provide an apparatus and device for use therein and a method for the ablation of tissue which incorporates a simplified tissue ablation device.

Another object of the invention is to provide an apparatus, device and method of the above character which can utilize a less expensive simplified tissue ablation device.

Another object of the invention is to provide an apparatus and device for use therewith in which a substantial portion of the device can be reused.

Another object of the invention is to provide a device of the above character in which the reusable portion includes the cabling connected to the device.

Another object of the invention is to provide a device of the above character in which the throwaway parts of the device have been reduced to a minimum.

Another object of the invention is to provide a device of the above character which is light in weight and which can be readily used.

Additional objects and features of the invention will appear from the following description in which the preferred embodiments are set forth in detail in conjunction with the accompanying drawings.

FIG. 1 is an isometric view of one embodiment of an apparatus and device for use therein for the ablation of tissue incorporating the present invention.

FIG. 2 is a cross-sectional view taken along the line 2—2 of FIG. 1.

FIG. 3 is a cross-sectional view taken along the line 3—3 of FIG. 2.

FIG. 4 is an enlarged detail view of the distal extremity of the device shown in FIGS. 1 and 2.

FIG. 5 is an isometric view of another embodiment of a device incorporating the present invention.

FIG. 6 is an isometric view of another embodiment of a device incorporating the present invention.

In general, the device for ablation of tissue is for use with the human hand and with a radio frequency controller providing a source of radio frequency energy and means for controlling the application of radio frequency energy to the device. It comprises a handle sized so as adapted to be grasped by the human hand and as proximal and distal extremities. A needle formed of conductive material and having proximal and distal extremities is provided. Means is provided for mounting he proximal extremity of the needle on the distal extremity of the handle so that it is insulated from the handle. The conductive means is carried by the handle and is connected to the needle and extends from the handle and is adapted to be coupled to the radio frequency controller for supplying radio frequency energy to the needle. Means is carried by the handle and is adapted to be coupled to the radio frequency power supply and controller for sensing the application of radio frequency energy to the tissue and for controlling the application of radio frequency energy to the needle.

More in particular, the apparatus 11 of device 12 for use therein for the ablation of tissue as shown in FIG. 1 includes the hand held device 12 and a radio frequency power supply and controller 13 as shown in block form.

The device 12 consists of a handle or housing 16 which is to size so that it is adapted to be grasped by the human hand or at least by two fingers of the human hand. The handle or housing 16 is formed of a suitable material such as a plastic which is molded into a desired shape as for example, generally cylindrical as shown in FIG. 1 and is provided with proximal and distal extremities 17 and 18. The handle 16 is provided with an outer surface 21 with a semi-hemispherical portion 21a provided on the proximal extremity, a cylindrical portion 21b extending from the proximal extremity for a distance of approximately 2-½", a tapered or conical portion 21c having a length of approximately 1-1/2" and a smaller diameter cylindrical portion 21d having a length of approximately ½". The handle 16 can be of a suitable diameter such as ½". It should be appreciated that if desired rather than it being circular in cross section, the handle 16 can be rectangular in cross section. A portion of the surface 21b is provided with a plurality of circumferentially extending annular grooves 22 spaced apart longitudinally of the central axis of the handle 16 to facilitate gripping of the handle by the fingers of a human hand. A pair of spaced apart annular recesses 23 and 24 is provided on which identification labels (not shown) can be placed.

A sharpened needle 26 is provided which has proximal and distal extremities 27 and 28. It is formed of a suitable conductive material such as stainless steel which is capable of delivering radio frequency energy. Means is provided for mounting the needle in the handle or housing 16 so that it is static or nondeployable. As shown in FIGS. 1 and 2, it is mounted on the distal extremity 18 by being molded directly into the plastic handle or housing 16. The proximal extremity 27 of the needle 26 is mounted in a carrier 31 formed of a suitable material such as plastic which is mounted within the handle 16 as shown in FIG. 2. A printed circuit board 32 is mounted on the carrier 31 immediately adjacent the proximal extremity 27 of the needle 26.

Conductive means 36 is carried by the handle and is connected to the needle and is adapted to be coupled to the radio frequency power supply and controller 13 for supplying radio frequency energy to the needle 26. Typically this conductive means takes the form of a single conductor 37 hereinafter described which is coupled to the needle 26 by suitable means such as solder and which extends proximally through the housing and to a flexible cable 41 secured to the proximal extremity of the handle 16. The flexible cable 41 carries a male adapter 42 which is adapted to be coupled to a female adapter (not shown) to a cable 44 to the radio frequency power supply and controller 13.

Means is carried by the handle or housing 16 and is adapted to be coupled to the radio frequency power supply and controller 13 for sensing the application of radio frequency energy as it is supplied by the needle 26 to the tissue in the human body for controlling the application of radio frequency energy to the tissue and consists of at least one device for sensing temperature and/or impedance. Thus as shown there are provided first and second thermocouples 46 and 47. In accordance with the present invention, the first thermocouple 46 as shown in FIG. 4 is mounted in the distal extremity 18 of the handle 16 and is provided for sensing the temperature of the tissue in the immediate vicinity of the thermocouple 46 adjacent to an intermediate portion of the needle 26 where it enters the handle 16, as for example approximately 20 millimeters from the end of the needle 26. First and second conductors 48 and 49 are provided which are connected to the thermocouple 46. If desired, the conductors 48 and 49 alternatively can be secured to the needle 26 by a shrink tube (not shown) secured to the handle 16 The other or second thermocouple 47 is mounted in the distal extremity 28 of the needle 26 and as shown can be supported by an epoxy 51 provided in a bore 52 in the needle 26 extending longitudinally of the needle 26. The epoxy 51 in addition to holding the thermocouple 47 seals off the lumen or bore 52. The thermocouple 47 senses the temperature of the tissue in the immediate vicinity of the distal extremity 28 of the needle 26. First and second conductors 53 and 54 connected to the thermocouple 47 extend proximally within the bore 52 of the needle 26 from the thermocouple 47. The conductors 48 and 49 and the conductors 53 and 54 extend proximally to the printed circuit board 32 as shown in FIG. 2 and terminate in three contacts 61, 62 and 63 provided on the printed circuit board 32 in which contact 62 is a common contact to which are bonded conductors 66, 67 and 68 which extend into the cable 41. Another contact 71 is provided on the printed circuit board 32 which is connected to the needle 26 by the conductor 37 which is also connected to a conductor 72 extending into the cable 41. These conductors 66, 67, 68 and 72 are connected into the radio frequency power supply and controller 13 and are utilized for supplying radio frequency energy to the needle electrode 26 and for the control of the radio frequency power supply and controller 13 in accordance with the parameters, i.e. temperatures, being sensed by at least one thermocouple and preferably both thermocouples 46 and 47.

Since the needle 26 is a static or nondeployable needle, the needle 26 upon manufacture of the device 12 can be selected to be of a suitable length projecting distally from the distal extremity 18 of the handle 16. Thus a needle having a length ranging from 15 to 30 mm and preferably approximately 20 mm can be readily provided. The needle can be of a certain size such as for example 23-gauge.

It should be appreciated that insulation can be extended on the needle so that a desired active length for the needle is provided for supplying radio frequency energy to the tissue.

Operation and use of the apparatus and the device for use therewith may now be briefly described as follows. Assuming that the device 12 has been connected to the radio frequency power supply and controller 13, the physician doing the desired tissue ablation procedure grasps the handle 16 of the device by the fingers of a hand or in the palm of the hand and with a straight needle 26 as shown in FIG. 1, the physician can utilize the handle to cause the needle to penetrate the tissue it is desired to ablate. The needle 26 is positioned so that the insulation engaging the proximal end of the needle 26 is well past the mucosal layers of the tissue, after which the radio frequency power supply and controller 13 can be turned on. This ensures that the mucosal layer will remain undamaged and will not be thermally ablated.

The needle 26 can be utilized as a unipolar device with a grounding pad (not shown) being provided on the patient as for example on the back of the patient to 15 complete the circuit for the radio frequency energy from the radio frequency power supply and the return to the radio frequency power supply 13. For example with a straight needle, the turbinates can be readily treated with the device 12. The treatment can be carried out for an appropriate length of time from 20 seconds to 5 minutes with the radio frequency energy being applied at the desired frequency, as for example a frequency of 580 kilohertz and a power level ranging from 5 to 50 watts. The shorter times are desirable where the size of the anatomical feature to be treated is small (such as the uvula) or where the tissue is highly hydrated or perfused. This helps to preserve anatomical tissue in the region to be ablated, as for example anatomical features which are then in cross-section (i.e., mucosal membranes). The thermocouples 46 and 47 can be utilized for automatically terminating the application of radio frequency power when a certain temperature in the tissue has been reached as sensed by either one or both of the thermocouples 46 and 47. The delivery of radio frequency energy to the needle 26 is terminated before the needle 26 is withdrawn from the tissue to avoid surface layer thermal damage. After the procedure has been completed, the physician can withdraw the device 12 and can further proceed with the procedure by inserting the needle 26 of the device 12 into another location using the same procedure. The foregoing steps can be repeated as necessary to complete the desired ablation of the tissue being treated.

In the case of some smaller anatomical features, the physician may use lower power levels to obtain a lesion of sufficient size without premature desiccation of the tissue surrounding the active electrode (needle). This lower rate of energy delivery is an important aspect of the present invention because it yields larger lesions and greater volume per penetration than would occur if the power settings were higher. In that case, rapid heating can result in loss of current delivery due to tissue desiccation. The reason the lower power settings result in larger lesions is that the hydrated tissue exhibits thermal conductivity at a fairly inefficient level, but is nonetheless somewhat thermally conductive. If the power setting is appropriate, the tissue is able to conduct the energy outwardly in the form of heat and the tissue immediately adjacent to the active electrode will be kept below the temperature of vaporization of the fluid within the tissue. When vaporization occurs, there is a fluctuation of the ohmic impedance to current low and the tissue rapidly desiccates, resulting in interruption of the circuit. This loss of current flow due to overheating of the tissue adjacent to the electrode needle can be an advantage in that it is a safety aspect of the present invention. For instance, in the event of inadvertent setting of the power at a high level, the rapid desiccation of the thin layer of cells in contact with the active electrode will break the circuit and act as a "biologic switch", cutting off current flow and preventing extensive tissue damage. Only by setting the power at lower levels, as for example 1 watt, can larger lesions be attained. Typically, power settings up to 15 watts are used with the type of device described in the present invention. Situations where power levels as high as 50 or 100 watts can occur where an electrode with a significantly larger surface area is used or where the tissue is highly perfused and the circulatory (blood flow) rate is high, resulting in efficient cooling of the tissue being treated.

For performing other tissue ablation procedures where a curved or bent needle 26 is desired, the needle 26 can be formed of a malleable material and can be bent in a suitable manner to the desired configuration to match the anatomy, as for example the treatment of tonsils, adenoids and sinus tissue. A straight needle can be utilized for treating the uvula.

After the device has been used, it can be disposed of because the device has been designed for a one time use even though the device is manufactured in such a way that it is sterilizable. However, sterilizing the same may be undesirable when it is difficult to ensure that sufficient sterilization has been accomplished and particularly if blood has coagulated on the needle 26 causing a protein buildup which may not be removed during the sterilization procedure. It should be appreciated as hereinbefore explained that the device can still be further simplified by using only one thermocouple. It is possible to utilize only one thermocouple by estimating the temperature gradient which normally occurs between the first and second thermocouples. By utilizing only the first thermocouple 46 it is possible to go to a solid wire for the needle 26 rather than a needle which has a lumen or bore therein.

In order to still further reduce the cost of the device utilized in connection with the present apparatus, another embodiment of the device is shown FIG. 5 in which the cable and connector are removably mounted on the device as part of the device so that they can be disconnected and only a part of the device disposed of after use. Thus as shown in FIG. 5 there is provided a device 81 which consists of a handle 82 sized to fit into a human hand and which has generally the same configuration as the handle 16, but which is generally rectangular in cross-section rather than circular. It is provided with proximal and distal extremities 83 and 84. The proximal extremity 83 of the housing has mounted therein the cable 41 hereinbefore described in the embodiment shown in FIGS. 1–4. The handle 82 is fabricated in two parts 82a and 82b with the part 82a forming the proximal extremity 83 and the part 82b forming the distal extremity 84. The printed circuit board 32 forming a part of the previous embodiment is also included in the present embodiment with the associated wiring (not shown) and is mounted in the reusable connector portion 82a of the handle 82. A connector assembly 86 is mounted in the two parts 82a and 82b and typically as shown can consist of a female connector 87 mounted in the reusable connector portion 82a and a male connector 88 mounted in the disposable portion 82b.

A needle 91 is mounted in the distal extremity 84 in the manner hereinbefore described in connection with the embodiment shown in FIG. 1. In the embodiment shown, the needle 91 is inclined at an angle with respect to the central axis of the handle 82 as for example at an angle of 45°. An insulating sleeve 92 is provided on the needle and has a length so that the exposed end of the needle 91 extends for a suitable distance as for example 15 to 30 mm and preferably approximately 20 mm. The insulating sleeve 92 is provided with a thread 93 on its exterior surface 94. The threads 93 can be relatively coarse, as for example a quarter pitch, so that a protective sleeve 96 with internal threads 97 in a bore 98 matching the threaded exterior surface 93 can be threaded onto and threaded off of the insulating sleeve 92 with four to five turns of the protective sleeve 96. The protective sleeve 96 can be formed of a suitable material such as plastic. The protective sleeve 96 has a length so that it will extend over the length of the insulating sleeve 92 and still provide adequate space for the needle 91 extending distally from the insulating sleeve 92.

It can be seen that by providing a threaded protective sleeve 96, the sleeve 96 can be rotated for removal of the same. This threaded arrangement is preferable to one which is mounted by a slip fit because a slip fit requires movement of the sleeve towards and away from the needle during pushing and pulling of the sleeve, making it possible for the physician using the same to inadvertently be punctured by the needle.

The device shown in FIG. 5 can be used in a manner very similar to that hereinbefore described with respect to the previous embodiment. After the device has been used, the portion 82b can be separated from the portion 82a and only the portion 82b disposed of after use. The remaining portion 82a with the cable 41 can be retained for future reuse. This part 82a can be readily sterilized if necessary and carries the carrier components which comprise the major expense in fabricating the handle 81. Thus it can be seen that such a construction makes it possible to further reduce the cost of the device utilized in the apparatus of the present invention.

Still another embodiment incorporating the device of the present invention is shown in FIG. 6 which is slightly more expensive than that shown in FIG. 5, but however retains as a separable part the connector and cable forming a part of the handle. Thus as shown in FIG. 6 there is provided a device 101 which is also sized to fit into the human hand but typically is larger so that it is adapted to be held in the palm of the hand while a finger or fingers are utilized for operating the device. The handle 102 as shown is rectangular in cross section and is provided with proximal and distal extremities 103 and 104 with the proximal extremity 103 comprising the reusable part and the distal extremity 104 comprising the disposable part. The handle or housing 102 is formed of a suitable material such as plastic with lower and upper parts 106 and 107 which are fastened together in a suitable manner such as by an adhesive or by ultrasonic bonding. A connector assembly 111 is provided for connecting the wires or conductors utilized in the device and consists of a male connector 112 provided in a distal extremity 104 and a female connector 113 provided in the proximal extremity or reusable portion 103. The male connector assembly is provided with a rectangular framework 116 formed of a suitable material such as plastic to prevent accidental contact with the pins 117 forming a part of the male connector assembly 112. The female connector assembly 113 is connected to the cable 41 connected to the reusable proximal part 103.

A retractable needle 121 is carried by the handle or housing 102 and is mounted on a slider 122 movable in slots 123 within the handle 102 from a distal extremity where the needle is in an extended position extending beyond a cylindrical insulation sleeve 124 forming a part of the handle 102 and a retracted position in which the needle is completely retracted within the insulation sleeve 124. Movement of the slider 122 is under the control of a circular knob 126 slidably mounted on the exterior of the handle or housing 102 and adapted to be grasped by a finger of the hand and particularly the thumb of the hand holding the device 101. The knob is provided with a centrally disposed circular recess 127 adapted to be engaged by the thumb of the holding hand. The knob 126 is provided with a depending stem 128 which extends through a slot 129 in the top cover 107. The slot 129 extends longitudinally of the top cover 107 along the central axis of the handle or housing 102. A printed circuit board 32 of the type hereinbefore described is mounted within the handle 102 and is provided with folded wires or conductors (not shown) which permit the slider 122 to move between extended and retracted positions while still continuing to receive information from the thermocouples and also to supply radio frequency energy to the needle 121.

Operation and use of the device 101 shown in FIG. 6 is very similar to that hereinbefore described. However, in many respects it is more user friendly than the other embodiments of the device herein disclosed. For example by providing a retractable needle 121, it is possible for the physician to position the needle in the desired position merely by engaging the knob 126 by the thumb of the hand while the same hand is holding the device to advance the needle 121 into the tissue to be treated. After the application of radio frequency energy in the manner hereinbefore described, the needle 121 can be retracted back into the handle 102 without danger of the physician being pricked by the needle. The major portion of the device can still be saved by separating the proximal portion 103 which carries the cable 41 from the distal portion 104 so that the distal portion can thereafter be disposed of after a one-time use.

From the foregoing it can be seen that there has been provided a device which can be utilized for ablation of tissue in connection with a radio frequency power supply and controller. The devices are small and adapted to be held by the human hand and are designed in such a manner so that the entire device or only a portion of the device can be disposed of after a one-time use. Static or retractable needles can be provided. The construction has been kept so that it is relatively simple to minimize the cost of construction and inexpensive materials have been utilized where possible.

What is claimed is:

1. A device for the ablation of tissue for use with the fingers of a human hand and a radio frequency power supply and controller providing a source of radio frequency energy and means for controlling the application of radio frequency energy to the device comprising a one-piece unitary handle having an exterior surface sized so that it is adapted to be grasped and supported by two fingers of the human hand and having proximal and distal extremities, a single conductive needle formed of a conducting material and having proximal and distal extremities, means for mounting the proximal extremity of the needle in a molded static position on the distal extremity of the handle so that it is the sole needle carried by the handle and is insulated from the handle and having a portion that extends distally of the handle, conductive means including a printed circuit board carried by the handle and connected to the needle and extending from the handle and adapted to be coupled to the radio frequency power supply and controller for supplying radio frequency energy to the needle and control means carried by the handle and adapted to be coupled to the radio frequency power supply and controller for sensing the application of radio frequency energy to the tissue for controlling the application of radio frequency energy to the needle, said control means being free of controls on the exterior surface of the handle.

2. A device as in claim 1 wherein said means for sensing the application of radio frequency energy to the tissue includes at least one thermocouple and conductors connected to said at least one thermocouple and adapted to be coupled to the radio frequency power supply and controller.

3. A device as in claim 2 wherein said means for sensing the application of radio frequency energy to the tissue includes an additional thermocouple and conductive means adapted to couple the additional thermocouple to the radio frequency power supply and controller.

4. A device as in claim 3 wherein the additional thermocouple is mounted in the distal extremity of the needle.

5. A device as in claim 2 wherein the proximal portion of the needle is inclosed within an insulating sleeve and wherein the at least one thermocouple is disposed in the insulating sleeve adjacent the needle.

6. A device as in claim 1 further including a removable protective sleeve extending over the needle.

7. A device as in claim 6 wherein the protective sleeve is threaded over the needle.

8. A device as in claim 1 wherein the needle is formed of a malleable material to permit bending of the needle to match the anatomy of the tissue to be treated.

9. A device as in claim 1 wherein said handle is in the form of a cylindrical body having a conical distal extremity, said cylindrical body having a plurality of longitudinally spaced-apart annular grooves formed therein proximal to the conical distal extremity to facilitate grasping of the handle by the fingers of the hand.

10. A device for the ablation of tissue for use with the human hand and a radio frequency power supply and controller providing a source of radio frequency energy and means for controlling the application of radio frequency energy to the device comprising a handle having an exterior surface with a width and sized so that is adapted to be grasped by the human hand and having proximal and distal extremities, a needle formed of a conducting material and having proximal and distal extremities, means for mounting the proximal extremity of the needle on the distal extremity of the handle so that it is insulated from the handle, conductive means carried by the handle and connected to the needle and extending from the handle and adapted to be coupled to the radio frequency power supply and controller for supplying radio frequency energy to the needle, control means carried by the handle and adapted to be coupled to the radio frequency power supply and controller for sensing the application of radio frequency energy to the tissue for controlling the application of radio frequency energy to the needle, said control means being free of controls on the exterior surface of the handle, said needle being slidably mounted in the handle for movement from an extended position to a retracted position in which the needle is enclosed within the handle and in the extended position has the distal extremity of the needle free of the handle, a single slider slidably mounted in the handle and secured to the proximal extremity of the needle, a knob having a generally circular recess therein adapted to receive a finger of the hand for resting within the recess and being mounted on the exterior of the handle, said knob extending substantially across the width of the handle, and means secured to the knob extending into the handle and engaging the slider whereby as the knob is advanced and retracted longitudinally of the handle, the needle is advanced from the handle and retracted into the handle.

11. A device as in claim 10 wherein said conductive means includes a connector assembly mounted in the handle and having first and second mating parts, said handle being separable into first and second parts with one mating part disposed in one part of the handle and the other mating part being disposed in the other part of the handle and wherein the means carried by the handle and adapted to be coupled to the radio frequency power supply and controller includes a cable secured to one of the first and second mating parts provided in the first part of the handle and in which the first part is reusable.

12. A device as in claim 11 wherein said conductive means carried by the handle and connected to the needle includes a printed circuit board mounted within the handle.

13. A method for the ablation of tissue in an anatomical feature, the anatomical feature being thin in cross section and having a mucosal layer overlying the tissue by the use of a device and a radio frequency power supply, the device comprising a handle having an exterior surface sized so as to be adapted to be grasped by and supported by two fingers of the human hand and having proximal and distal extremities and a needle formed of a conductive material and having proximal and distal extremities, means for mounting the proximal extremity of the needle on the distal extremity of the handle and control means carried by the handle and free of external controls on the exterior surface of the handle and adapted to be coupled to the radio frequency power supply for controlling the application of radio frequency power to the needle for the ablation of tissue, the method comprising supplying a needle having a conformation matching the anatomy of the tissue to be treated, inserting the needle through the mucosal layer into the tissue by the use of two fingers grasping the handle while viewing over the exterior surface of the handle the insertion of the needle into the mucosal layer so that the insulating layer carried by the needle extends beyond the mucosal layer and into tissue, supplying radio frequency energy to the needle at a low wattage ranging from 1 to 5 watts for a period of time ranging from 20 seconds to 5 minutes to cause ablation of the tissue and to preserve the tissue in the anatomical feature that is thin in cross-section, sensing the temperature of the tissue in the vicinity of the distal extremity of the needle, automatically terminating the delivery of radio frequency energy to the needle when a predetermined temperature has been reached in the tissue in the vicinity of the needle and thereafter withdrawing the needle from the tissue to avoid thermal damage to the mucosal layer.

* * * * *